United States Patent [19]

della Valle et al.

[11] Patent Number: 5,696,099
[45] Date of Patent: Dec. 9, 1997

[54] TOPICAL PREPARATIONS FOR THE TREATMENT OF ACNE AND ACNEIFORM DERMATITIS

[75] Inventors: Francesco della Valle; Roberto Cerini, both of Padua; Gabriella Calderini, Carrara San Giorgio, all of Italy

[73] Assignee: Lifegroup S.p.A., Rome, Italy

[21] Appl. No.: 229,025

[22] Filed: Apr. 18, 1994

[51] Int. Cl.[6] .................................. A61K 31/725
[52] U.S. Cl. .................. 514/56; 514/626; 514/574; 424/722
[58] Field of Search .................. 514/56, 626, 574; 424/722

[56] References Cited

U.S. PATENT DOCUMENTS

| | | | |
|---|---|---|---|
| 4,711,780 | 12/1987 | Fahim | 424/145 |
| 4,977,250 | 12/1990 | Diaz et al. | 536/21 |
| 5,116,963 | 5/1992 | Del Bono et al. | 536/21 |
| 5,422,115 | 6/1995 | Horrobin | 424/422 |

FOREIGN PATENT DOCUMENTS 0550008  7/1993  European Pat. Off. .

OTHER PUBLICATIONS

J. Lab. Clin. Med., vol. 115, No. 1, pp. 43–51 (1990), Dol et al.

British Medical J., vol. 292, p. 28 (1986), Boyle et al.

Dermatol. Venerol., 126, 1//10: 29–33 (1991), M. Nazzaro Poro et al.

Primary Examiner—Marianne M. Cintins
Assistant Examiner—M. Moezie
Attorney, Agent, or Firm—Hedman, Gibson & Costigan, P.C.

[57] ABSTRACT

Topical Preparations for the treatment of acne and acneiform dermatitis containing as active principle therapeutically active quantities of N,N'bis (2-hydroxyethyl) nonandiamide together with dermatansulfate lithium salt, having molecular weight ranging from 2000 to 7000, combined with suitable excipients and/or diluents.

18 Claims, 4 Drawing Sheets

FIG. 1

CUTANEOUS DESQUAMATION

| Days after treatment | Treated Animals | | | | | | Control Group | | | | | |
|---|---|---|---|---|---|---|---|---|---|---|---|---|
| | 1 | 2 | 3 | 4 | 5 | 6 | 1 | 2 | 3 | 4 | 5 | 6 |
| 1 | +++ | +++ | +++ | +++ | +++ | +++ | +++ | +++ | +++ | +++ | +++ | +++ |
| 2 | +++ | +++ | +++ | +++ | +++ | +++ | +++ | +++ | +++ | +++ | +++ | +++ |
| 3 | + | + | + | + | + | + | +++ | +++ | +++ | +++ | +++ | +++ |
| 4 | − | − | − | − | − | − | +++ | +++ | +++ | +++ | +++ | +++ |
| 5 | − | − | − | − | − | − | ++ | ++ | ++ | ++ | ++ | ++ |
| 6 | − | − | − | − | − | − | ++ | ++ | ++ | ++ | ++ | ++ |
| 7 | − | − | − | − | − | − | ++ | ++ | ++ | ++ | ++ | ++ |
| 8 | − | − | − | − | − | − | + | + | + | + | + | + |
| 9 | − | − | − | − | − | − | + | + | + | + | + | + |
| 10 | − | − | − | − | − | − | + | + | + | + | + | + |
| 11 | − | − | − | − | − | − | + | + | + | + | + | + |
| 12 | − | − | − | − | − | − | − | − | − | − | − | − |
| 13 | − | − | − | − | − | − | − | − | − | − | − | − |
| 14 | − | − | − | − | − | − | − | − | − | − | − | − |
| 15 | − | − | − | − | − | − | − | − | − | − | − | − |
| 16 | − | − | − | − | − | − | − | − | − | − | − | − |
| 17 | − | − | − | − | − | − | − | − | − | − | − | − |
| 18 | − | − | − | − | − | − | − | − | − | − | − | − |
| 19 | − | − | − | − | − | − | − | − | − | − | − | − |
| 20 | − | − | − | − | − | − | − | − | − | − | − | − |

FIG. 2

PRESENCE OF COMEDONES

| Days after treatment | Treated Animals | | | | | | Control Group | | | | | |
|---|---|---|---|---|---|---|---|---|---|---|---|---|
| | 1 | 2 | 3 | 4 | 5 | 6 | 1 | 2 | 3 | 4 | 5 | 6 |
| 1 | +++ | +++ | +++ | +++ | +++ | +++ | +++ | +++ | +++ | +++ | +++ | +++ |
| 2 | +++ | +++ | +++ | +++ | +++ | +++ | +++ | +++ | +++ | +++ | +++ | +++ |
| 3 | +++ | +++ | +++ | +++ | +++ | +++ | +++ | +++ | +++ | +++ | +++ | +++ |
| 4 | +++ | +++ | +++ | +++ | +++ | +++ | +++ | +++ | +++ | +++ | +++ | +++ |
| 5 | +++ | +++ | +++ | +++ | +++ | +++ | +++ | +++ | +++ | +++ | +++ | +++ |
| 6 | ++ | ++ | ++ | ++ | ++ | ++ | +++ | +++ | +++ | +++ | +++ | +++ |
| 7 | + | + | + | + | + | + | +++ | +++ | +++ | +++ | +++ | +++ |
| 8 | + | + | + | + | + | + | +++ | +++ | +++ | +++ | +++ | +++ |
| 9 | + | + | + | + | + | + | +++ | +++ | +++ | +++ | +++ | +++ |
| 10 | + | + | + | - | - | - | +++ | +++ | +++ | +++ | +++ | +++ |
| 11 | + | + | + | - | - | - | +++ | +++ | +++ | +++ | +++ | +++ |
| 12 | + | + | + | - | - | - | ++ | ++ | ++ | ++ | ++ | ++ |
| 13 | + | + | + | - | - | - | ++ | ++ | ++ | ++ | ++ | ++ |
| 14 | + | + | + | - | - | - | + | + | + | + | + | + |
| 15 | - | - | - | - | - | - | + | + | + | + | + | + |
| 16 | - | - | - | - | - | - | + | + | + | + | + | + |
| 17 | - | - | - | - | - | - | + | + | + | + | + | + |
| 18 | - | - | - | - | - | - | + | + | + | + | + | + |
| 19 | - | - | - | - | - | - | + | + | + | + | + | + |
| 20 | - | - | - | - | - | - | - | - | - | - | - | - |

CUTANEOUS ELASTICITY (YOUNG INDEX) - EVALUATION AFTER 10 DAYS AFTER TREATMENT

* = Treated
@ = Controls

FIG. 4

Clinical Evaluation in patients affected by acneic lesions of different type

| Patients treated | 10 (M = 2; F = 8) |
|---|---|

| Age (medium) | 20.3 years (range=12 - 28) |
|---|---|

| Clinical diagnosis | comedonal acne | n°1 |
|---|---|---|
| | papular acne | n°4 |
| | nodulo-cystic acne | n°3 |
| | conglobate acne | n°2 |

| Grading (medium) | 2.5 (range 0.25 - 6) |
|---|---|

| Duration of treatment | 30 days |
|---|---|

| Improvement (percentage) on | |
|---|---|
| non-inflamed lesions (open and closed comedones) | 19% |
| superficial inflamed lesions (papules and pustules) | 42% |
| profound inflamed lesions (nodules and cysts) | 38% |

| Evaluation by the patient | |
|---|---|
| week | n°1 |
| sufficient | n°3 |
| good | n°4 |
| excellent | n°2 |

TOPICAL PREPARATIONS FOR THE TREATMENT OF ACNE AND ACNEIFORM DERMATITIS

FIELD OF THE INVENTION

The present invention relates to topical compositions for the treatment of acne and acneiform dermatitis containing as active principle therapeutically effective quantities of N,N'bis (2-hydroxyethyl) nonandiamide together with dermatansulfate lithium salt, having molecular weight ranging from 3000 to 8000, combined with suitable excipients and/or diluents.

PRIOR ART DISCLOSURE

The acne pathology includes a variety of non-homogeneous affections, having in common the follicular localization.

The most common affection is acne vulgaris, whose aetiology is not known, even if exists the hypothesis of an involvement of predisposing genetic factors.

The pathogenesis is accompanied by a series of events acting in successive order and each of them can justify particular clinical aspects of acne.

The primary modification is an accelerated keratinization of the external epitelial guaina of the pilifer follicles with production of a more dense keratinous material than normally, that accumulates inside the follicle, forming a comedo with consequent sebum retention.

A second predisposing factor is the abundant production of sebum: the disease is observed in the sebaceous follicles prevailingly during the periods of life when the sebaceous glands are particularly active.

The third genetic factor is of infective origin and consists in the early colonization of the pilifer follicles with bacteria.

The acne pathology is thus a polymorphous affection manifesting with comedones, papules, pustules and sometimes with nodules, cysts and phlegmon infiltrates, pitted or in more severe cases, also hypertrophic scars.

The outcome of the disease is variable and the heterogenicity of the signs requires often associated therapies for topical as well as general administration and the most indicated products are those which are able of reducing sebum production/secretion or those with antibacterial property.

Azelaic acid (AZA) or nonandianoic acid is a saturated bicarboxylic nine carbon atoms acid derived from oxidation of linoleic acid. This molecule shows to have bacteriostatic and bactericidal activity against a variety of aerobic and anaerobic microorganisms which normally are present on acne-bearing skin.

Topical application of azelaic acid in formulation of 20% creams, induces a marked reduction of the cutaneous and intrafollicular bacterial flora present on the skin—in addition to a reduction of the fatty acids content of the skin surface lipids, whereas there seems not to be a significant alteration of the sebaceous gland morphology or of the sebum production.

Moreover, administration of the same quantities of the above-mentioned active principle, shows an antikeratinising effect as well on normal skin, as on acne-affected skin, an effect due to the decreased synthesis of filaggrin, keratin filament aggregating protein, inducing thus a reduction of follicular hyperkeratosis.

More recent evidences have furthermore proved a specific sebum regulating role of topically administered lithium (J. Boile et al. British Medical Journal, vol. 292, 1986). This effect seems due to the ability of lithium to block the release of fatty acids and to its inhibitory effect on the synthesis of prostaglandines.

Azelaic acid and lithium, even if free from toxicity, may, at the normally utilized therapeutic concentration, cause irritative phenomena of the skin in ca. 10% of the treated patients.

Moreover, the acneic eruption is often associated and aggravated by an inflammatory condition which is usually treated with cortisonic drugs.

Since the remission of such events generally requires long treatment periods, the side effects of glucocorticoids assume particular importance especially with respect to the young age of the subjects under treatment.

In this context, the need was felt to have products, which are able to display their effect already after short periods of treatment and which are free from side effects.

SUMMARY

The Applicant has now inexpectedly found topical compositions which are capable to treat successfully acne without giving the disadvantages of the pharmaceutical topical compositions of the prior art.

The present invention relates to therapeutic compositions for topical use in the treatment of acne and acneiform dermatitis, containing as active principle therapeutically effective quantities of N,N'-bis(2-hydroxyethyl) nonandiamide together with a therapeutically effective quantity of dermatansulfate lithium salt, having molecular weight ranging from 3000 to 8000, in combination with suitable eccipients and/or diluents.

Such compositions, having a sebum regulating activity associated to an antiinflammatory and antibacteric effect, are as a matter of fact able to accelerate the resolution of the acneic affections, utilizing total dosages of the above mentioned active principles 10 times lower compared to those contained in the already known antiacne formulations, and, at the same time, maintaining elasticity and trophism of the tissues.

Moreover, as an effect of the synergisms of the above-mentioned active principles, much shorter times were observed for the resolution of the acneic phenomenon compared to the already known and currently available formulations.

The above-mentioned active principles are utilized also for the preparation of dermocosmetic formulations.

BRIEF DESCRIPTION OF THE DRAWINGS

FIG. 1 shows the cutaneous desquamation observed in animals treated with the material under evaluation.

FIG. 2 shows the presence of comedones in treated and control animals.

FIG. 4 shows the observed improvement on lesions from treatment.

DETAILED DESCRIPTION OF THE INVENTION

Figure 3:
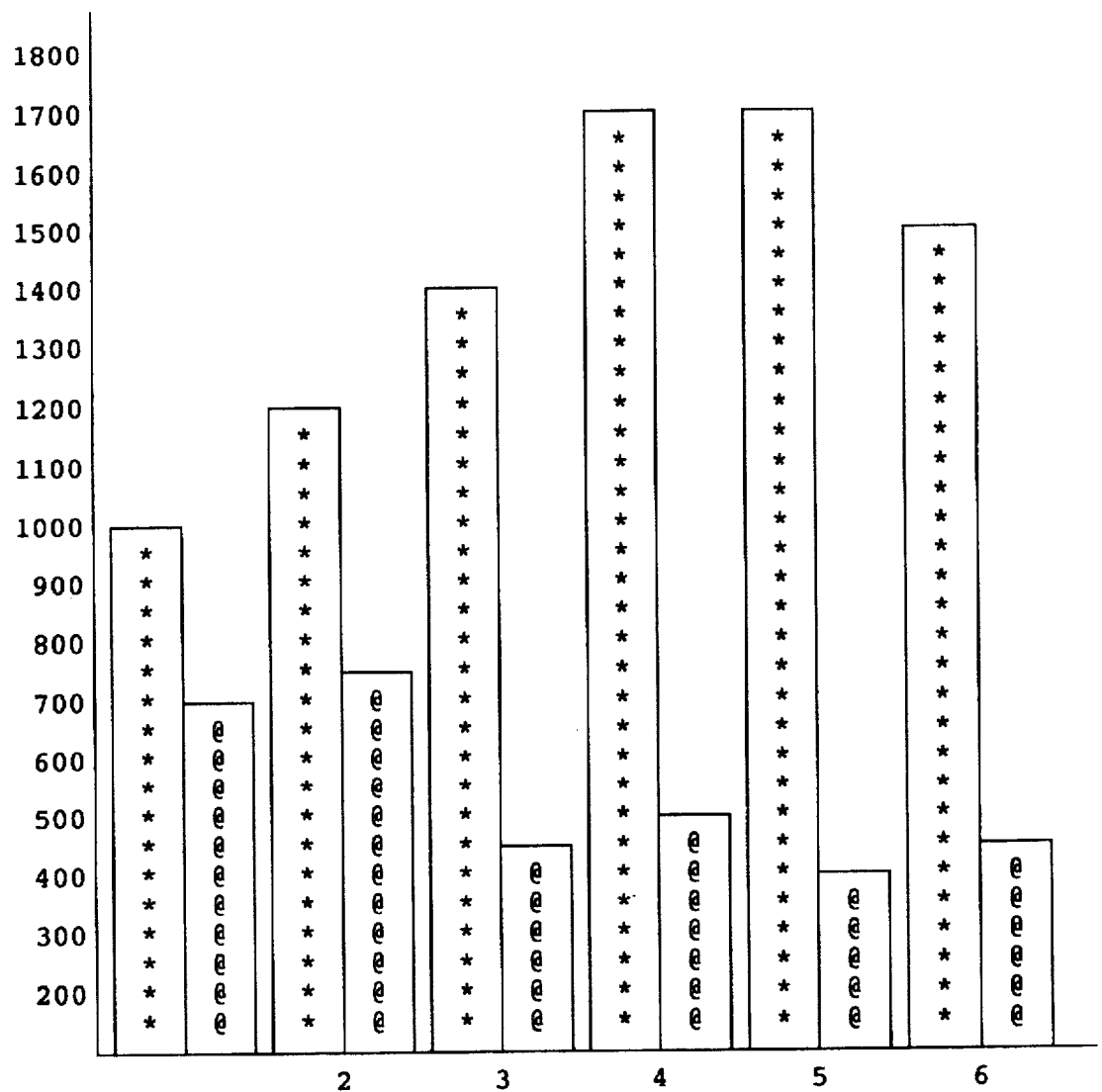
FIG. 3 shows the elasticity of the skin of treated and control animals.

The alcanolamide of azelaic acid, which is one of the two active principles contained in the therapeutic compositions described in the present invention, and its pertinent therapeutic activity, consisting in the inhibition of mast cell degranulation induced by diverse stimuli, and consequently endowed with an antiinflammatory effect, limiting also the increase of capillary permeability resulting from the aforesaid inflammation, have been described in the previous EPA No. 92121864.0; U.S. patent application Ser. No. 07/998, 792, now abandoned, filed by the same Assignee.

The second active principle used for the above mentioned therapeutic compositions, dermatansulfate lithium salt, which is an innovative molecule further relating to the present invention, is prepared by a process consisting in an elution of dermatansulfate sodium salt previously solubilized in distilled water through a column filled with a cationic-exchange resine generated Li+ ion form at 4° C.

Dermatansulfate characterized by the above-mentioned molecular weight shows to be free from significant anticoagulant activity (F. Dol et al., J. Lab. Clin.med., 1990, 151:43–51) and is prepared by a process of controlled chemical depolimerization as described in U.S. patent application Ser. No. 4,977,250.

The pharmaceutical and dermocosmetic compositions, according to the present invention, optionally contain also other active principles such as lithium in form of a lithium salt which is different from dermatansulfate, preferably lithium citrate, or under form of the hydroxic corrispondent, having sebum-regulating activity, o-phenylphenole having antibacterial and keratinolytic activity, methyl and/or ethyl parahydroxybenzoate with antibacteric activity. The formulations relating to the present invention are preferably in the form of gel, lotions or in the form of pads soaked up with the solution.

As diluent is generally used water, and for the preparation of gel, as a thickening and emulsionating agent preferably is used a carboxyvinylic polymer, such as carboxypolymethylene, available on the market with the trade mark CARBOM®.

N,N'bis(2-hydroxyethyl) nonandiamide in concentrations ranging from 1% to 2% is preferably used for the dermocosmetic formulations. For the dermocosmetic formulations, dermatansulfate lithium salt with mean molecular weight within the above-mentioned range, is preferably used in concentrations ranging from 0.05 to 0.15% of weight/whole weight (w/w) of the above described composition.

The other compound, salt or hydroxic containing lithium ion optionally contained in the compositions according to the present invention, is utilized in concentrations lower than 3%, preferably ranging from 1% to 2%.

O-phenylphenol, when present in the compositions according to the present invention, is utilized in quantities generally ranging from 0.10 to 0.30% weight/whole weight (w/w).

Ethyl- or methyl-parahydroxy benzoate, if present, are generally contained in the topical compositions according to the present invention in quantity ranging generally from 0.05 to 0.20%.

When present, the thickening agent is generally contained in quantities ranging from 0.50 to 0.70% weight/whole weight (w/w) of the composition.

The biologic activity relating to these new formulations make them particularly interesting in case of Acne juvenilis, Acne vulgaris in the different comedonal, papular, nodulocystic manifestations and in all situations where it is important to associate with sebum-regulating and antibacteric phenomena a strong antiinflammatory effect without on the other hand diminishing the condition of elasticity and hydratation of the tissues, contrarily to what is observed after long periods of treatment with the currently available topical formulations, which lead to even visible alterations of the hydratation of the more or less primarily affected cutaneous areas of the skin.

The topical compositions according to the present invention may also be proposed for the so-called acne from chemical or physical agents and for the folliculitis and moreover for the treatment of the seborrheic skalp, alopecia, seborrheic alopecia and seborrheic dermatitis.

The treatment with the pharmaceutical and dermocosmetic compositions described in the present invention, comprises the application of the said composition from 2 to 5 times a day for variable periods, depending on the pathology and anyway not less than 4 weeks.

The following examples for the preparation of dermatansulfate lithium salt according to the present invention and for the preferred topical compositions are supplied for illustrative purposes but do not limit in any way the present invention.

Example 1

Preparation of low molecular weight dermatansulfate lithium salt.

25,2 g of dermatansulfate sodium salt, having molecular weight of about 7000 dalton, are solubilized in 200 ml of distilled water. The solution is eluted in a column cooled at 40C., containing 120 ml of cationic-exchange resine Dowex®. 50×8 generated in Li+ form. The eluate free from sodium is frozen and lyophilized. The reaction yield is 23,3 g.

The chemical-physical properties of the product dermatansulfate lithium salt are:

| | |
|---|---|
| physical state | white amorphous powder |
| raw formula | $C_{14}H_{19}NO_{14}SLi_2$ |
| molecular weight | 7000 dalton |
| elemental analysis | C = 35.68%; H = 4.06%; N = 2.97%; S = 6,80%; Li = 2,95% (calculated) |
| | C = 35.55%; H = 4.10%; N = 2.92%; S = 6.80%; Li = 2.90 (found) |
| water solubility | >10 mg/ml |

Example 2

| 2 a. Gel formulation | |
|---|---|
| N,N-bis(2 hydroxyethyl)-nonandiamide | 2% |
| dermatansulfate lithium salt | 0.10% |
| Hydrated Lithium (solution 5%) | 1.8% |
| o-Phenylphenol | 0.20% |
| p-methyl-hydroxybenzoate | 0.10% |
| p-ethyl-hydroxybenzoate | 0.10% |
| Carbomer | 0.70% |
| Dem. Water | 95% |

The said composition is prepared according to the following method:

a) the gelold base is prepared (water and Carbomer 940), under vacuum, maintaining a good agitation until Carbomer is completely swelled and homogenized.

b) The different active principles are added gradually, stirring until complete dissolution and homogeneization.

c) Once completed the addition of the different active principles agitation is continued for further 30–60 minutes, restoring from time to time the vacuum and afterwards the liquid is drained into the containers provided for this purpose.

The gel obtained in this manner, is characterized by a medium consistence, opalescent aspect, a light aromatic smell, and pH 6,5±0,5; viscosity is about 2800 cps, determined with viscometer Contraves®., mod.TV, 3, 200 rot/min. rotor. at 20° C. Density is about 1.0030, determined with pycnometer suitable for measuring pasty solids, at 20° C. referred to water density at the same temperature.

| 2 b. Lotion formulation | |
|---|---|
| Water dem. | 89.5% |
| N,N-bis(2-hydroxyethyl)nonandiamide | 2% |
| Citric Acid lithium salt | 2.0% |
| o-phenylphenole | 0.20% |
| Dermatansulfate lithium salt | 0.10% |
| p-methyl hydroxybenzoate | 0.10% |
| p-ethyl hydroxybenzoate | 0.10% |
| Polysorbate 20 | 6.00% |

The pH is gently restored using HCl at 6.6±0.5. The obtained solution is perfectly disperded, has a clear aspect and light aromatic smell, pH 6.6±0.5.

| 2 c. Soaked pads formulation | |
|---|---|
| N,N bis(2-hydroxyethyl)nonandiamide | 1% |
| dermatansulfate lithium salt | 0.10% |
| hydrated lithium (sol. 5%) | 0.270% |
| o-phenylphenole | 0.20% |
| p-methyl hydroxybenzoate | 0.20% |
| p-ethyl hydroxybenzoate | 0.20% |
| Carbomer | 0.100% |
| Polysorbate 20 | 6.000% |
| Dem. Water | 92.030% |

Cottonwool pads of diameter 5 cm are soaked up with the above described solution. The solution results omogeneously distributed on the pad which appears non-oily, with light aromatic smell, pH 6.5±0.5.

BIOLOGIC ACTIVITY

Experimental model

In a group of 12 albino New Zealand rabbits weighing 2,5–2,8 kg (6 males and 6 females) a severe condition of comedogenesis is induced, treating topically the inner surface of the ear pinna two times a day for 15 days which isopropylmiristate.

The rabbits have been normally fed and kept in an usual stable.

Treatment of the animals

The rabbits are divided into two groups of 6 animals each (3 males and 3 females). To the inner surface of the ear pinna of the animals of the treated group a thin layer of the preparation described above in Example 2.a is applied every day for 7 days.

The animals of the control groups have not been treated.

Experimental parameters

1. Cutaneous desquamation

The evaluation has been performed through attribution of the following score:

30+++ severe desquamation

20++ medium desquamation

10+ light desquamation

1– normal skin

2. Cutaneous elasticity has been evaluated through "plasto elasticity checker", considering as parameter the Young index which is proportional to the elasticity of the skin.

3. Presence of comedones: the extent of the lesion has been quantified through attribution of the following score:

30+++ presence of big comedones

20++ presence of medium large comedones; implicated area not very extended

1– complete restoration of the normal conditions of the skin

Results:

The results of the above mentioned tests are reported respectively in FIG. 1,2 and 3.

The remarkable desquamation of the skin, caused in phase of induction, has disappeared completely in the animals treated with the material under evaluation, already after 3 days of application, such desquamation has been observed for other 10 days in the animals of the control group (FIG. 1)

The elasticity of the skin completely disappeared in the animals of the control group during the whole period, has been restored in the animals of the treated group in ca. 6 days (FIG. 3).

A severe condition of comedones persisted for 10 days in the animals of the control group whereas it had significantly disappeared in the group of treated animals already after seven days of application. Three days after the last treatment, the skin of the inner side of the right ear of the treated animals appeared to be normal in 3 of 6 rabbits, in the other three, the skin presented bigger and blacker comedones than normal which disappeared on day 12 of the treatment (FIG. 2).

These results show a very early effect of the treatment and show beyond an important anticomedogenic activity also a particularly interesting effect on the tissue elasticity.

Clinical Evaluation

A preliminary clinical evaluation has been performed on 10 cases (2 male and 8 female) aged between 12 and 28 (medium age 20–23), suffering from comedonal acne (n=1); papulopustular acne (n=4); nodulo-cystic ache (n=3); conglobate acne (n=2).

The patients have been treated for 30 days (treatment 2 times a day with a thin layer of composition 2.a. described above).

Results

The composition under discussion has been administered in form of gel (composition 2.a.). It has shown improvement on superficial inflamed lesions (42%) and deep inflamed lesions (38%). The treatment furthermore has been considered from good -to- excellent in 6 patients from 10, as shown by the data reported in FIG. 4.

The clinical data are particularly interesting with regard to the statistically significant effect at early times.

The clinical studies performed with azelaic acid highlighted as a matter of fact an effect at 6 months (M. Nazzaro Porto et al., G.It. Dermatol. Venerol., 1991, 126, 1/10: 29–33).

The treatment with the composition according to the present invention, allows moreover to avoid the disadvantages linked to repeated cycles of antibiotic and hormonal therapies.

We claim:

1. A therapeutic composition for topical use for the treatment of acne and acneiform dermatitis, containing as active principles a therapeutically effective amount of N,N'-bis-(2-hydroxyethyl)-nonandiamide and of dermatansulfate lithium salt having molecular weight ranging from 3000 to 8000 daltons in combination with suitable excipients and/or diluents.

2. A therapeutic composition for topical use for the treatment of acne and acneiform dermatitis, containing as active principles therapeutically effective amounts of: (a) N,N'-bis-(2-hydroxyethyl)-nonandiamide; (b) dermatansulfate lithium salt having a molecular weight ranging from 3000 to 8000 daltons; (c) at least a lithium compound selected from the group consisting of lithium citrate and lithium hydroxide; and (d) at least an antibacterial selected from the group consisting of o-phenyl-phenol, methyl-parahydroxybenzoate and ethyl-para-hydroxybenzoate, in combination with suitable excipients or diluents.

3. The composition according to claims 1 or 2 in form of a gel, of lotions or in the form of soaked up pads.

4. The composition according to claims 1 or 2, wherein the diluent is water.

5. The composition according to claim 3, in form of a gel which includes carboxypolymethylene as a thickening and emulsionating agent.

6. The therapeutic composition according to claim 1, wherein N,N'-bis-(2-hydroxyethyl)-nonandiamide is present in quantity from 1 to 2% by weight and the dermatansulfate lithium salt is present in a quantity of from 0.05 to 0.15% by weight.

7. The composition according to claim 2, wherein N,N'-bis-(2 hydroxyethyl) nonandiamide is present in quantities from 1 to 2% by weight, the dermatansulfate lithium salt in quantities from 0.05 to 0.15% by weight, lithium citrate or lithium hydroxyde are present in quantities from 1 to 2% by weight, o-phenylphenol is present in quantities from 0.10 to 0.30% by weight, methyl- and ethyl parahydroxybenzoate are present in quantities from 0.05 to 0.20% by weight.

8. The composition according to claim 5, wherein carboxypolymethylene is included in quantities from 0.50 to 0.70% by weight.

9. A therapeutic method for the treatment of Acne juvenilis, acne vulgaris, acne induced by chemical or physical agents, folliculitis, seborrheic scalp and seborrheic dermatitis comprising topical administration of a composition according to claims 1 or 2.

10. A therapeutic composition for topical use for the treatment of acne and acneiform dermatitis, which consists essentially of therapeutically effective amounts of: (a) N,N'-bis-(2-hydroxyethyl)-nonandiamide,; (b) of dermatansulfate lithium salt having a molecular weight ranging from 3000 to 8000 daltons; (c) at least a lithium compound selected from the group consisting of lithium citrate and lithium hydroxide; and (d) at least an antibacterial selected from the group consisting of o-phenyl-phenol, methyl-parahydroxybenzoate and ethyl-parahydroxybenzoate, in combination with suitable excipients or diluents.

11. A therapeutic method for the treatment of Acne juvenilis, acne vulgaris or acne induced by chemical or physical agents comprising topical administration of a composition according to claims 1 or 2.

12. A therapeutic method for the treatment of Acne juvenilis, acne vulgaris, ache induced by chemical or physical agents, folliculitis, seborrheic scalp and seborrheic dermatitis, said method comprising topical administration of a composition according to claim 2.

13. A therapeutic method for the treatment of Acne juvenilis according to the method of claim 12.

14. A therapeutic method for the treatment of acne vulgaris according to the method of claim 12.

15. A therapeutic method for the treatment of acne induced by chemical or physical agents according to the method of claim 12.

16. A therapeutic method for the treatment of folliculitis according to the method of claim 12.

17. A therapeutic method for the treatment of seborrheic scalp according to the method of claim 12.

18. A therapeutic method for the treatment of seborrheic dermatitis according to the method of claim 12.

* * * * *